United States Patent
Roederer

(10) Patent No.: US 7,282,224 B1
(45) Date of Patent: Oct. 16, 2007

(54) PAIN RELIEF COMPOSITION

(75) Inventor: Joy E. Roederer, Santa Monica, CA (US)

(73) Assignee: Guthy-Renker Corporation, Santa Monica, CA (US)

( * ) Notice: Subject to any disclaimer, the term of this patent is extended or adjusted under 35 U.S.C. 154(b) by 0 days.

(21) Appl. No.: 11/450,648

(22) Filed: Jun. 9, 2006

(51) Int. Cl.
*A01N 65/00* (2006.01)

(52) U.S. Cl. .................................. 424/725

(58) Field of Classification Search .............. None
See application file for complete search history.

(56) References Cited

U.S. PATENT DOCUMENTS

| | | | |
|---|---|---|---|
| 4,761,288 A | 8/1988 | Mezei | |
| 4,897,269 A | 1/1990 | Mezei | |
| 4,937,078 A | 6/1990 | Mezei et al. | |
| 5,562,924 A | 10/1996 | Perrier et al. | |
| 5,780,047 A | 7/1998 | Kamiya et al. | |
| 5,889,057 A * | 3/1999 | Barrett et al. | 514/570 |
| 6,048,545 A | 4/2000 | Keller et al. | |
| 6,197,823 B1 | 3/2001 | Barr et al. | |
| 6,239,180 B1 | 5/2001 | Robbins | |
| 6,248,788 B1 | 6/2001 | Robbins et al. | |
| 6,277,398 B1 | 8/2001 | Caruso | |
| 6,284,797 B1 | 9/2001 | Rhodes | |
| 6,383,524 B2 * | 5/2002 | Tao | 424/725 |
| 6,387,398 B1 | 5/2002 | Vollhardt et al. | |
| 6,482,432 B2 | 11/2002 | Wang | |
| 6,491,902 B2 | 12/2002 | Shefer et al. | |
| 6,495,596 B1 | 12/2002 | Keller | |
| 6,573,302 B1 | 6/2003 | Holt et al. | |
| 6,579,543 B1 | 6/2003 | McClung | |
| 6,593,370 B2 | 7/2003 | Tamura et al. | |
| 6,649,178 B2 | 11/2003 | Mohammadi et al. | |
| 6,653,352 B2 | 11/2003 | Barr et al. | |
| 6,689,399 B1 | 2/2004 | Dickson | |
| 6,740,327 B2 | 5/2004 | Yu et al. | |
| 6,780,443 B1 | 8/2004 | Nakatsu et al. | |
| 6,812,254 B1 * | 11/2004 | Barr et al. | 514/627 |
| 6,844,368 B1 | 1/2005 | Roberts et al. | |
| 6,858,232 B2 | 2/2005 | Verbiscar | |
| 6,864,261 B2 | 3/2005 | Gharagozloo et al. | |
| 6,998,421 B2 | 2/2006 | Keller et al. | |
| 2002/0012640 A1 | 1/2002 | Mohammadi et al. | |
| 2002/0034543 A1 | 3/2002 | Kirschner et al. | |
| 2002/0198260 A1 | 12/2002 | Keller et al. | |
| 2003/0072842 A1 | 4/2003 | Johnson et al. | |
| 2003/0109580 A1 | 6/2003 | Keller et al. | |
| 2003/0113356 A1 | 6/2003 | Deckner et al. | |
| 2003/0175333 A1 | 9/2003 | Shefer et al. | |
| 2003/0235629 A1 * | 12/2003 | Hornack et al. | 424/722 |
| 2004/0047930 A1 | 3/2004 | Webbe et al. | |
| 2004/0062779 A1 | 4/2004 | Whittemore et al. | |
| 2004/0062823 A1 | 4/2004 | Obukowicz et al. | |
| 2004/0081680 A1 | 4/2004 | Pesce et al. | |
| 2004/0082654 A1 | 4/2004 | Pesce et al. | |
| 2004/0086476 A1 | 5/2004 | Hammer et al. | |
| 2004/0110835 A1 | 6/2004 | Keller et al. | |
| 2004/0147605 A1 | 7/2004 | Onuki et al. | |
| 2004/0151678 A1 | 8/2004 | Barrere et al. | |
| 2004/0180081 A1 | 9/2004 | Angel et al. | |
| 2004/0191237 A1 | 9/2004 | Davidson et al. | |
| 2004/0197429 A1 | 10/2004 | Obukowicz et al. | |
| 2004/0228803 A1 | 11/2004 | Smith et al. | |
| 2005/0031547 A1 | 2/2005 | Tamarkin et al. | |
| 2005/0037038 A1 | 2/2005 | Gupta et al. | |
| 2005/0058672 A1 | 3/2005 | Gupta | |
| 2005/0148910 A1 | 7/2005 | Gregory et al. | |
| 2005/0149810 A1 | 7/2005 | Gregory et al. | |
| 2006/0110415 A1 * | 5/2006 | Gupta | 424/401 |

OTHER PUBLICATIONS

ALCiS HEALTH, Inc., The Science of ALCiS website www.alcis.com, Nov. 15, 2006, website pp. 1-4.

* cited by examiner

*Primary Examiner*—Michael Meller
*Assistant Examiner*—Qiuwen Mi
(74) *Attorney, Agent, or Firm*—Cislo & Thomas, LLP

(57) ABSTRACT

Disclosed is a pain relief composition comprising an effective amount of a nerve inhibiting component, including capsaicin, a capsaicinoid or a capsaicin analogue, which numbs or inhibits the nerve endings that signal pain, in combination with at least one of the following: an effective amount of an inflammation control component which is designed to reduce immediate pain and discourage future pain in the joints and muscles; an effective amount of a cooling component; an effective amount of a heat minimizing or blocking component; an effective amount of a circulation increasing component which effectuates better penetration of the actives to the skin and nerves; and an effective amount of a soothing and anti-inflammatory complex for the joints and/or muscles comprising Glucosamine sulfate or HCl, *Zingiber officiniale* (Ginger Root) extract, Methyl sulfonylmethane (MSM), *Polygonum cuspidatum* (Mexican Bamboo) extract, *Aloe barbadensis* leaf, and *Salix alba* (white willow) bark extract. Additionally, the composition includes an encapsulation or entrapment system for a timed release delivery.

1 Claim, No Drawings

PAIN RELIEF COMPOSITION

BACKGROUND

1. Field of the Invention

The present invention relates to compositions and methods of pain relief.

2. Description of the Related Art

The use of capsaicin is known for the treatment of a number of pain disorders, including rheumatoid arthritis, osteoarthritis, diabetic neuropathy, psoriasis, pruritus (itching), cluster, headache, post-surgical pain, oral pain, and pain caused by injury, amongst others. Capsaicin works by depleting a compound called Substance P, which is a neuropeptide that functions as a neurotransmitter and promotes pain perception, from the nerve terminal fibers. However, the topical use of capsaicin also causes an intense burning or stinging sensation, when first applied, which may be intolerable for some. Additionally, it may take more than a day or two for effectuating actual pain relief, and for the intense burning to stop.

SUMMARY

A pain relief composition, according to the present invention comprises an effective amount of a nerve inhibiting component, including capsaicin, a capsaicinoid or a capsaicin analogue, which numbs or inhibits the nerve endings that signal pain, in combination with at least one of the following: an effective amount of an inflammation control component which is designed to reduce immediate pain and discourage future pain in the joints and muscles; an effective amount of a cooling component; an effective amount of a heat minimizing or blocking component; an effective amount of a circulation increasing component which effectuates better penetration of the actives to the skin and nerves; and an effective amount of a soothing and anti-inflammatory complex for the joints and/or muscles comprising Glucosamine (sulfate or HCl), Zingiber officiniale (Ginger Root) extract, Methyl sulfonylmethane (MSM), Polygonum cuspidatum (Mexican Bamboo) extract, Aloe barbadensis leaf, and Salix alba (white willow) bark extract.

Additionally, according to a preferred embodiment, at least some of the active agents including capsaicin are encapsulated or entrapped for a timed release delivery. This composition provides immediate and long lasting relief while minimizing the discomfort associated with capsaicin.

OBJECTS OF THE INVENTION

It is an object of the present invention to provide a pain relief composition and a pain relief method to provide immediate, long-lasting and cumulative long-term relief from pain and inflammation of sore or stressed muscles and joints.

It is another object of the present invention to provide a pleasantly fragranced, pain relief formulation which can be applied topically.

It is yet another object of the present invention to provide a pain relief composition, comprising capsaicin, which is effective and comfortable to apply to the skin.

It is yet another object of the present invention to provide a soothing, anti-inflammatory complex for the joints and muscles, which can be used in combination with other pain relief agents.

It is another object to provide a pain relief composition containing cooling agents, which minimize the sensation of pain and signal effectiveness.

Other objects and advantages of the present invention will be apparent from a review of the following specification.

DETAILED DESCRIPTION

The detailed description set forth below is intended as a description of exemplary embodiments and is not intended to represent the only forms in which the exemplary embodiments may be constructed and/or utilized. The description sets forth the functions and the sequence of steps for constructing and/or operating the exemplary embodiments. However, it is to be understood that the same or equivalent functions and sequences which may be accomplished by different exemplary methods are also intended to be encompassed within the spirit and scope of the invention.

As used herein, "safe and effective amount" means a sufficient amount of a compound, composition or other material described by this phrase to significantly induce a positive modification in the condition being treated, but low enough to avoid undue side effects (e.g., significant skin irritation or sensitization), within the scope of sound judgment of the skilled person. The safe and effective amount of the compound, composition or other material may vary with the particular person being treated, factoring the age and physical condition of the biological subject being treated, the severity of the condition, the duration of treatment, the nature of concurrent therapy, the specific compound, composition, or other material employed, the particular carrier utilized, and the factors within the knowledge and expertise of the skilled person.

A pain relief composition, according to the present invention comprises an effective amount of a nerve inhibiting or pain relief component, including capsaicin, a capsaicinoid or a capsaicin analogue, which numbs or inhibits the nerve endings that signal pain, in combination with at least one of the following:

an effective amount of an inflammation control component which is designed to reduce or relief inflammation, swelling, redness, fever and/or pain in the joints and muscles associated with inflammation;

an effective amount of a cooling component which provides a cooling sensation for soothing, pain relief, and as a signal of efficacy;

an effective amount of a heat minimizing or blocking component which provides a decrease in the skin heat sensation;

an effective amount of a circulation increasing component which effectuates better penetration of the actives to the skin and nerves; and an effective amount of a joint and/or muscle soothing and anti-inflammatory complex comprising: Glucosamine, Zingiber officiniale (Ginger Root) extract, Methyl sulfonylmethane (MSM), Polygonum cuspidatum (Mexican Bamboo) extract, Aloe barbadensis leaf, and Salix alba (white willow) bark extract.

The pain relief composition further includes a unique delivery system, comprising particles having an average particle size of below 100 microns, wherein at least a portion of at least one active is encapsulated or entrapped. This system is designed to deliver controlled release over time to help maximize immediate and long term pain relief, and is especially effective for minimizing the side effect of burning associated with capsaicin.

Pain Relief Component:

The nerve inhibiting or pain relief component includes a capsaicin, a capsaicinoid or a capsaicin analogue. Preferably, the composition includes up to 0.75% capsaicin, and more preferably about 0.025% capsaicin. This agent works by depleting Substance P and disables the transmission of pain messages to the brain for meaningful long-term relief.

Other pain relief agents which may be used in combination with capsaicin include, but are not limited to, lidocaine, aloe vera, MSM, Willow Bark (salix alba) Extract, menthol, glucosamine, chondroitin, ginger, gotu kola, ginkgo, juniper, arnica extract, feverfew extract, St. John's wort extract, kava kava extract, nettle leaf, acetylsalicylic acid, Bala, black cohosh, black snakeroot, bugbane, squawroot, bupleurum, calendula, camphor, cayenne, devil's claw root, licorice, marjoram, meadow sweet, passion flower, quercetin, salicinum, wild yam, wintergreen, wood betony, wormwood, and essential oils such as Ylang Ylang, Coriander, Tea Tree, and Valerian Root, evening primrose, lavender, Roman chamomile, and emu.

Inflammation Control Component:

The inflammation control component includes at least one agent selected from the following: Linoleic acid, Ginger Root extract, willow bark, Polygonum cuspidatum (Mexican Bamboo) extract, Aloe vera, Geanium oil, Oleic Acid, coriander oil, Bisabolol, Geranium oil, MSM, Glucosamine, and willow herb. Other inflammation control agents which may be used include, but are not limited to, emu oil, chondroitin, arnica extract, grape seed extract, marigold extract, nettle leaf extract, Roman chamomile oil, bluebottle extract, St. John's wort, witch hazel extract, feverfew extract, barley grass, black cohosh, black snakeroot, bugbane, squawroot, Boswellia, borage, bromelain, burdock, calendula, cayenne, dandelion, devil's claw root, DHEA (dehydroepiandosterone), Echinacea, EFAs (essential fatty acids), elderflower, evening primrose oil, flaxseed, ginkgo, ginseng, Hawthorne, kaempferol, licorice, life root, golden Senecio, squaw weed, golden groundsel, cocash weed, coughweed, ragwort, golden ragwort, grundy swallow, linden, marjoram, meadow sweet, NDGA, neem, Padma 28, quercetin; turmeric, wild yam, wormwood, yucca and combinations thereof.

Cooling Component:

The cooling component is intended to provide a cooling sensation for soothing, pain relief, and as a signal of efficacy. This component also decreases the discomfort and burning associated with capsaicin and pain perception. Preferred cooling agents include at least one agent selected from the following: Menthone glycerin acetal, menthyl lactate, ethyl menthane carboxamide, methyl diisopropyl propionamide, peppermint oil, menthol, and menthoxypropanediol. Menthone glycerin acetal is available under the trade name Frescolat MGA® SYMRISE, and the combination of menthyl lactate, ethyl menthane carboxamide, and methyl diisopropyl propionamide is available under the trade name NanoSal™ SalCool™ SALVONA (containing lauryl laurate, ethyl menthane carboxamide, methyl diisopropyl propionamide, menthyl lactate, and hydroxyethyl behenamodopropyl dimoniumchloride). Preferably, the cooling component combines the ingredients SalCool™, which may be present at a level of between 0.5-20%, and more preferably at a level of between 2-5%, and Frescolat™, which may be present at a level of between 0.1-10%. More preferably, a combination of 2% SalCool and 10% Frescolat is used. Other preferred cooling agents include Peppermint oil at approximately 0.01-1.0%, menthoxypropanediol at approximately 0.01-1.0%, menthyl lactate at approximately 0.5-10%, and Menthol at below 0.1%. Other cooling agents known in the art may also be used.

Heat-Minimizing or Blocking Component:

The heat-minimizing or blocking component is intended to provide a decrease in the skin heat perception or sensation, and thus decrease the discomfort associated with capsaicin. A preferred heat minimizing agent is Zanthoxylum Alatum Extract, and its analogs, derived from Sichuan Peppercorn. This agent is available under the trade name Zanthalene® LIPO CHEMICALS. The Zanthoxylum Alatum Extract may be present at a level of 0.05-2.0% with a preferred level of 0.1% (Zanthalene® is supplied as a 20% solution from Lipo Chemicals, so the preferred level is 0.5% of a 20% solution). Other components known in the art to minimize thermal sensitivity or block or absorb heat sensation may also be used.

Circulation-Increasing Component:

The circulation increasing component is intended to effectuate increased oxygen uptake, and better penetration of the actives to the skin and nerves. Preferred agents include at least one agent selected from Gynostemma pentaphyllum extract and Ginseng. More preferably, the circulation increasing component combines these two agents. A combination of Gynostemma Pentaphyllum Extract and Panax Ginseng root Extract is commercially available under the trade name Actigen®O2 ACTIVE ORGANICS. This combination is designed to increase circulation in the capillaries of the skin resulting in increased oxygen update and better delivery and penetration of the pain relieving ingredients to the nerves and skin. Actigen® O2 may be present at a level of up to approximately 10%, with the preferred level of 0.5%.

Other circulation increasing agents, which may be used include but are not limited to lime tree extract, marigold extract, feverfew extract, St. John's wort extract, arnica extract, Roman chamomile oil, nettle extract, marigold extract, grape seed extract, witch hazel extract, arjuna, Bala, benzoin, bilberry, black pepper, blue gum eucalyptus, MSM, blue-bottle extract, coriander oil, blue vervain, borneol, butcher's broom, cayenne, cypress, geranium, ginger, ginkgo, grape seed proanthocyanidin extract (GSPE), Hawthorne, L-arginine, lemon, lemon grass, linden flowers, niaouli, oat straw, orange blossom, passion flower, thyme, violet, Peru balsam, pine, prickly ash bark, rose oils, rosemary, Spanish sage, spruce, white birch, yohimbe and combinations thereof.

Joint and/or Muscle Soothing and Anti-Inflammatory Complex:

The present invention further provides a joint and/or muscle soothing and anti-inflammatory complex comprising: Glucosamine (either sulfate or hydrochloride complex, and either sodium or potassium salt), Ginger Root extract, MSM, Polygonum cuspidatum (Mexican Bamboo) extract, Aloe barbadensis leaf, and Salix alba (white willow) bark extract.

Glucosamine is found naturally in the body and a building block of healthy cartilage, and is an amino sugar, which is a key building block to the synthesis of glycosaminoglycans, hyaluronic acid and proteoglycans. This agent encourages joints to become more elastic and resilient. This agent may be present up to 10%, and more preferably at a level of approximately 0.01%.

MSM works synergistically with Glucosamine to reduce muscle and joint pain, swelling and inflammation. This agent may be present at a level of up to 5% and is preferably present at a level of approximately 0.01%.

Ginger root extract is a natural herbal alternative to COX-2 inhibitors, and inhibits COX-2 enzymes that cause painful joints and muscles, thus reducing inflammation and pain.

This agent may be present at a level of 0.05-2.0%, and more preferably at a level of about 0.1-0.5%.

Polygonum cuspidatum extract scavenges excess nitric oxide (NO) to help reduce inflammation as a contributing factor to pain. This agent may be present at a level of 0.1-2.0%, with a preferred level of 0.25%.

Aloe barbadensis leaf juice extract helps to reduce joint and muscle pain associated with arthritis, as well as pain related to tendonitis and injuries. It further provides anti-inflammatory and pain-relieving benefits. This agent may be present at a level of up to 20%, and more preferably at a level of approximately 0.05%.

Salix alba (white willow) bark extract is rich in tannins and salicylic acid-like materials. The freshly prepared extract has been reported to have analgesic, antiseptic, astringent, anti-pyretic and anti-inflammatory properties. This agent may be present at a level of up to 2%, and more preferably at a level of approximately 0.1%.

Other soothing and/or anti-inflammatory agents which may optionally be used include cinnamon oil for warming sensation at approximately 0.01-2.0%, Camphor below 0.1%, Hydrocortisone below 0.25%, and Lidocaine below 0.5%.

Other Benefiting Agents:

A topical composition prepared in accordance with the present invention may comprise other skin benefiting or carrier components, including, but not limited to conditioning agents, skin protectants, antioxidants, viscosity modifying agents, film formers, emollients, surfactants, solubilizing agents, preservatives, fragrance, chelating agents, foaming or antifoaming agents, opacifying agents, stabilizing agents, pH adjustors, absorbents, anti-caking agents, slip modifiers, various solvents, solubilizing agents, denaturants, bulking agents, emulsion stabilizing agents, suspending agents, colorants, binders, conditioning agent-emollients, surfactant emulsifying agents, biological products, cosmetic soothing aids, and/or combinations thereof.

Delivery System:

The composition of the present invention utilizes a delivery system wherein at least a portion of the actives are encapsulated or entrapped, for a timed release delivery. This provides for a controlled and extended effect of the actives. Entrapment further allows the actives time to travel down to the site of discomfort before being fully released for a targeted effect. Additionally, the composition may contain combinations of encapsulated or entrapped actives, and free actives, such that an immediate effect is provided by the free ingredient(s) and a sustained effect is achieved through the encapsulated/entrapped ingredient(s).

Preferably, capsaicin is at least partially encapsulated or entrapped, for mitigating its potential for burning and discomfort. Other actives which offset the effects of capsaicin, such as other analgesics, cooling agents, anti-inflammatory agents, and/or soothing agents, may be at least partially encapsulated as well. As such, actives which counteract the discomfort associated with capsaicin, may be released in time with the capsaicin to offset the discomfort.

The preferred encapsulation/entrapment system utilizes liposomes, plant-derived microspheres, and/or nanospheres. The smaller particle size, of below approximately 100 microns, makes these delivery systems ideal for penetration into the skin.

Liposomal microspheres which are 100-1500 nanometers or 0.1 to 1.5 microns in size with a mean size of 0.4 microns, and composed of bilayer forming phospholipids (unilamellar and/or multilamellar liposome vesicles), may be formed separately as an intermediate, or in situ during the processing of the entire formula. (See U.S. Pat. Nos. 4,897,269; 4,937,078; 4,485,054; and 4,761,288). Liposome encapsulation is preferred since liposomes are composed of membrane-like lipid layers, which makes them more bio compatible, as compared to other delivery systems. Additionally, liposomes are slightly larger than nanospheres, so they will not penetrate as deep into the skin.

Plant derived microspheres, which are polysaccharides of about 20-100 microns in size, are available from COLETICA, under the trade name Phytospheres®. (See U.S. Pat. No. 5,562,924; EPO 630,287). Examples of such plant derived microspheres which may be used with the present invention include Phytosphere®CGUT002A, encapsulating lidocaine, (containing Water, Butylene Glycol, Caprylic/Capric Triglyceride, Ethylparaben, Methylparaben, Propylparaben, Carbomer, Lidocaine, and Acacia Seegal Gum), and Phytosphere®CGUT003A, encapsulating capsaicin, (containing Water, Butylene Glycol, Caprylic/Capric Triglyceride, Ethylparaben, Methylparaben, Propylparaben, Carbomer, Capsaicin, and Acacia Senegal Gum).

Nanospheres, which are single or multi-component, solid hydrophobic spheres with an average particle size of 0.01 to 1 micron, are available from SALVONA, under the tradename NanoSal™. (See U.S. Pat. No. 6,491,902; and AU 2003248704) Examples of Nanospheres which may be used with the present invention include NanoSal Capsaicin™ (containing 1% Capsaicin, Euphorbia Cerifera (Candelilla) Wax, Hydroxyethyl Behenamidopropyl Dimonium Chloride, PEI-10, and Water) and NanoSal SalCool™ (containing Menthyl Lactate, Lauryl Lactate, Trimethyl Isopropylbutamide, Ethyl Menthane Carboxamide, and Hydroxyethyl Behenamodopropyl Dimonium Chloride).

A topical pain relief composition comprising liposomes containing actives formed in situ, is prepared according to Example 1, as follows:

EXAMPLE 1

| Item | WT | Procedure |
| --- | --- | --- |
| Phase 1: | | |
| 1. Water (Part I) | 56.96% | Phase 1: In a suitable kettle add Water (Part I). |
| 2. Carbomer (Carbopol Ultrez 10 ™ NOVEON) | 0.30% | Disperse well Carbopol Ultrez 10 at Room |
| 3. Methylparaben | 0.25% | Temperature. Start heating to 70° C. ± 5° C. and add methylparaben. Mix well to dissolve. Continue to mix until uniform. |

-continued

| Item | WT | Procedure |
|---|---|---|
| Phase 2: | | |
| 4. Isopropyl Palmitate (Liponate IPP ™ LIPO CHEMICALS) | 1.00% | Phase 2: In a separate kettle add materials 4-12. Start mixer and heat to 70° C. ± 5° C., mix until uniform. When both phases are at 70° C.-75° C. and uniform, add Phase 2 to Phase 1 and mix well. Homogenize until a fine emulsion is formed. Stop homogenizer and continue to mix at 70-75° C. for 30 minutes more. Cool to 40° C. |
| 5. Caprylic/Capric Triglyceride (Botanester ™ BOTANIGENICS) | 1.00% | |
| 6. Arlacel ™ 60 (sorbitan monostearate) | 1.00% | |
| 7. (Cyclomethicone) Dow Corning 245 Fluid ™ DOW CORNING | 2.00% | |
| 8. Stearic Acid (LIPO CHEMICALS) | 1.50% | |
| 9. Cetyl Alcohol (LIPO CHEMICALS) | 3.50% | |
| 10. Lipomulse ™ 165 LIPO CHEMICALS (Glyceryl stearate, PEG-100 stearate) | 4.00% | |
| 11. Propylparaben (UEFICH) | 0.10% | |
| 12. Emersol 213 Oleic Acid (Unifat SL ™ COGNIS CORPORATION) | 0.10% | |
| Phase 3: | | |
| 13. Water (Part II) | 10.00% | Phase 3: In a separate vessel add Water (Part II), Capsaicin and Precept. Heat to 50-55° C., mixing well until uniform. Add the remaining Phase 3 ingredients, and mix well until uniform. Force cool to 40° C. Add Phase 3 materials to the main batch and mix well. |
| 14. Precept (hydroxylated lecithin SOLAE) | 1.00% | |
| 15. Capsaicin 40% (PREMIER SPECIALTIES) | 0.07% | |
| 16. Actiphyte ® of Willow Bark ACTIVE ORGANICS (containing Butylene Glycol, Water, and *Salix alba* (Willow) Bark Extract) | 0.50% | |
| 17. Actiphyte ® of Ginger Root ACTIVE ORGANICS (containing Propylene Glycol, Water, and *Zingiber officinale* (Ginger) Root Extract) | 0.50% | |
| 18. Canadian Willow Herb Extract ROSS ORGANICS (*Epilobium angustifolium* Extract) | 0.50% | |
| 19. Aloe Vera Powder | 0.05% | |
| 20. Glucosamine Sulfate Sodium (NOVEL INGREDIENT SERVICES) | 0.01% | |
| 21. MSM (Dimethyl Sulfone from HALTON HEALTH) | 0.01% | |
| 22. Actigen O2 ® ACTIVE ORGANICS (containing Glycerin, Water, *Gynostemma pentaphyllum* Extract, and *Panax ginseng* Root Extract) | 0.50% | |
| 23. Zanthalene ® 20% Solution LIPO CHEMICALS (*Zanthoxylum alatum* Extract) | 0.50% | |
| 24. Mexican Bamboo Extract (Butylene Glycol, Water, and *Polygonum cuspidatum* Extract from PREMIER SPECIALTIES) | 0.25% | |
| Phase 4: | | |
| 25. Nanosal Salcool ® 4653 SALVONA (Menthyl Lactate, Lauryl Laurate, Methyl Diisopropyl Propionate, Ethyl Menthane Carboxamide, and Hydroxyethyl Behenamidopropyl Dimonium Chloride) | 2.00% | Phase 4: Add materials 25-31 one at a time and mix well until uniform. |
| 26. Emersol 315 | 0.10% | |
| 27. S5-27855 Coriander fragr. Allergen Free (PREMIER SPECIALTIES) | 0.70% | |
| 28. Triethanolamine 99% (UNIVAR USA) | 0.30% | |
| 29. Phenoxyethanol (ASHLAND) | 1.00% | |
| 30. Germall ® 115 (Imidazolidinyl UREA) | 0.30% | |
| 31. Frescolat MGA ® SYMRISE (Menthone Glycerin Acetal) | 10.00% | |

The above described composition is a cream, containing liposome entrapped capsaicin, and entrapped actives comprising Aloe, MSM, Ginger, Glucosamine sulfate, Gynostemma pentaphyllum extract, Panax ginseng root extract, Willow bark extract, Willowherb extract, Polygonum Cuspidatum, and Zanthoxylum alatum extract. The formulation also contains nanosphere encapsulated cooling agents present in the Nanosal™ Salcool™, and further contains a free cooling agent, Menthone Glycerin Acetal.

Liposomal capsaicin concentrate containing other actives, which is an intermediate, stand-alone product for use in the formulation of a pain cream composition of the present invention, is prepared according to Example 2, as follows:

EXAMPLE 2

| Item | WT | Procedure |
|---|---|---|
| Phase 1: | | |
| 1. Purified Water | 21.55% | In container A, add and mix materials 1-4. Heat to |
| 2. Actiphyte ® of Willow Bark ACTIVE ORGANICS (containing Butylene Glycol, Water, and *Salix alba* (Willow) Bark Extract) | 10.00% | 70° C. ± 5° C. Then add materials 5-10. Mix until dissolved and completely uniform. |
| 3. Aciphyte ® of Ginger Root ACTIVE ORGANICS (containing Propylene Glycol, Water, and *Zingiber officinale* (Ginger) Root Extract) | 10.00% | |
| 4. Willow Herb Extract ROSS ORGANICS (*Epilobium angustifolium* Extract) | 10.00% | |
| 5. Methylparaben | 0.25% | |
| 6. Propylparaben | 0.10% | |
| 7. Carbopol Ultrez 10™ NOVEON | 1.00% | |
| 8. Glucosamine Sulfate Sodium (NOVEL INGREDIENT SERVICES) | 0.20% | |
| 9. MSM (Dimethyl Sulfone from HALTON HEALTH) | 0.20% | |
| 10. Aloe Vera Powder | 1.00% | |
| Phase 2: | | |
| 11. Precept. (hydroxylated lecithin SOLAE) | 20.00% | When the contents in container A are dissolved and |
| 12. Capsaicin 40% (PREMIER SPECIALTIES) | 1.40% | uniform, add the precept., mix until completely |
| 13. Actigen O2 ® | 10.00% | dissolved and homogenous. Force cool to 50° C., then |
| 14. *Zanthoxylum alatum* Extract (Zanthalene ® 20% Solution LIPO CHEMCIALS) | 10.00% | slowly add materials 12-15 into the container A. Mix until uniform. Continue to force cool container A to |
| 15. Mexican Bamboo (Butylene Glycol, Water, and *Polygonum cuspidatum* Extract from PREMIER SPECIALTIES | 5.00% | below 40° C. When the contents in container A are below 40° C., add materials 16 and 17. Mix until uniform. |
| 16. Imidazolidinyl Urea | 0.30% | |
| 17. Triethanolamine | 1.00% | |

A pain cream prepared using the liposomal capsaicin concentrate of Example 2, is prepared according to Example 3, as follows:

EXAMPLE 3

| Item | WT | Procedure |
|---|---|---|
| Phase 1: | | |
| 1. Isopropyl Palmitate (Liponate IPP LIPO CHEMICALS) | 1.00% | In container A, add and mix materials 1-9. Heat to 70° C. ± 5° C. until all solids are completely dissolved |
| 2. Caprylic/Capric Triglyceride (Botanester BOTANIGENICS) | 1.00% | and homogenous. |
| 3. Sorbitan Stearate (Liposorb S LIPO CHEMICALS) | 1.00% | |
| 4. Cyclomethicone (Dow Corning 245) | 2.00% | |
| 5. Stearic Acid (LIPO CHEMICALS) | 1.50% | |
| 6. Cetyl Alcohol (LIPO CHEMICALS) | 3.50% | |
| 7. Botanimulse 165 ™ (BOTANIGENICS) | 4.00% | |
| 8. Propylparaben (UEFICH) | 0.095% | |
| 9. Oleic Acid (Unifat SL (Emersol 213 Oleic Acid) COGNIS CORPORATION) | 0.10% | |
| Phase 2: | | |
| 10. Purified Water | 67.9825% | In container B, add and mix materials 10-12. Heat to |
| 11. Carbopol Ultrez 10 ™ | 0.25% | 70° C. ± 5° C. until all solids are completely dissolved |
| 12. Methylparaben | 0.2375% | and homogenous. When the content in both containers A and B are at 70° C. ± 5° C. and all solids are completely dissolved, transfer the contents of container A into container B. Run homogenizer until fine emulsion is formed. Continue to mix for 30 minutes. Force cool to below 40° C. |

-continued

| Item | WT | Procedure |
|---|---|---|
| Phase 3: | | |
| 13. Salcool ™ Nanosal Salcool ® 4653 SALVONA(Menthyl Lactate, Lauryl Laurate, Methyl Diisopropyl Propionate, Ethyl Menthane Carboxamide, and Hydroxyethyl Behenamidopropyl Dimonium Chloride) | 2.00% | When the combined Phases 1 and 2 in container A are at least or below 40° C., slowly add and mix materials 13-20 into container A. Mix until uniform. |
| 14. Linoleic Acid (COGNIS) | 0.10% | |
| 15. Coriander Fragrance (PREMIER SPECIALTIES) | 0.70% | |
| 16. Phenoxyethanol | 1.00% | |
| 17. Imidazolidinyl Urea | 0.285% | |
| 18. Frescolat MGA ® SYMRISE (Menthone Glycerin Acetal) | 10.00% | |
| 19. Liposomal Capsaicin Concentrate | 5.00% | |
| 20. Triethanolamine | 0.25% | |

The composition of the present invention may be used by rubbing over an area to be treated. A recommended method of use is to rub the cream over the entire area, until the cream disappears, and use about 2 to 3 times daily, and preferably not more than 3-4 times daily. Additionally, the amount of cream used may be gradually increased with each successive application. The topical composition of the present invention may be formulated in any acceptable topical vehicle, including gel, ointment, liquid rub, wax, paste, etc.

While the pain relieving composition which is formulated for topical application, the compositions may also be made ingestible, using components which are safe for human consumption. Such ingredients may include D-Glucosamine (as HCl or Sulfate complex, and either sodium or potassium salt), ginger root, Salix Alba (white willow bark), MSM, Aloe Barbadensis Leaf Juice, polygonum cuspidatum Extract, Oleic Acid, and Linoleic Acid. In its ingestible form, the composition may be formulated with suitable excipients including, dicalcium phosphate, microcystaline cellulose, stearic acid, croscarmellose sodium, magnesium stearate, silica, and combinations thereof. Additionally, a pain relieve system may include using both a topical and an ingestible formulation.

In closing, it is to be understood that the exemplary embodiments described herein are illustrative of the principles of the present invention. Additionally, the functions identified for certain components mentioned herein are not intended to limit the components' scope of use. Other modifications that may be employed are within the scope of the invention. Thus, by way of example, but not of limitation, alternative configurations may be utilized in accordance with the teachings herein. Accordingly, the description is illustrative and not meant to be a limitation thereof.

What is claimed is:

1. A topical pain relief composition comprising:
   a) an effective amount of a pain relieving component selected from the group consisting of capsaicin, a capsaicinoid, a capsaicin analogue, and combinations thereof;
   b) an effective amount of an inflammation control component which is designed to reduce immediate pain and discourage future pain in the joints and muscles;
   c) an effective amount of a cooling component comprising approximately between 0.5-20% of a mixture containing menthyl lactate, ethyl menthane carboxamide, and methyl diisopropyl propionamide, and approximately between 0.1-10% of menthone glycerin acetal;
   d) an effective amount of a heat absorbing component;
   e) an effective amount of a circulation increasing component which effectuates better penetration of the active components to the skin and nerves; and
   f) an effective amount of a soothing and anti-inflammatory complex for the joints and/or muscles comprising Glucosamine, *Zingiber off'iciniale* (Ginger Root) extract, Methyl sulfonylmethane (MSM), *Polygonum cuspidatum* (Mexican Bamboo) extract, *Aloe barbadensis* leaf, and *Salix alba* (white willow) bark extract, wherein at least a portion of said composition, including at least a portion of said pain relieving component, is entrapped in a delivery system comprising particles having an average particle size of less than 100 microns, said delivery system effectuating an extended and time controlled release of the entrapped composition at the site of pain, to mitigate discomfort associated with capsaicin and enhance the efficiency of the entrapped active components.

* * * * *